United States Patent [19]

Mann et al.

[11] Patent Number: 5,531,668
[45] Date of Patent: Jul. 2, 1996

[54] INFLATABLE PALMAR BLADDER

[75] Inventors: Donaerl B. Mann; Don M. Mann, both of High Springs, Fla.

[73] Assignee: D'Mannco, Inc., High Springs, Fla.

[21] Appl. No.: 384,517

[22] Filed: Feb. 6, 1995

[51] Int. Cl.$^6$ ........................................ A61F 5/00
[52] U.S. Cl. .................. 602/13; 602/21; 602/22; 482/44; 482/47; 482/113
[58] Field of Search .................. 602/13, 20, 21, 602/22; 601/40; 128/118.1, 836, 837, DIG. 20; 2/16; 482/44, 47, 113

[56] References Cited

U.S. PATENT DOCUMENTS

| | | |
|---|---|---|
| 3,901,225 | 8/1975 | Sconce ........................ 602/13 |
| 5,020,515 | 6/1991 | Mann . |
| 5,056,504 | 10/1991 | Mann . |
| 5,152,740 | 2/1992 | Harkensee . |
| 5,297,541 | 3/1994 | Hersey ........................ 601/40 |
| 5,383,827 | 1/1995 | Stern ........................... 602/13 |

*Primary Examiner*—Richard J. Apley
*Assistant Examiner*—Kim M. Lee
*Attorney, Agent, or Firm*—Herbert W. Larson

[57] ABSTRACT

A longitudinal, substantially cylindrical shaped inflatable bladder for inserting within the palmar region of a constricted hand to extend the fingers outwardly and to promote exercise of the constricted hand. The bladder has a channel for receiving an end portion of a static hand orthosis permitting the inflatable bladder to be attached to a static hand orthosis. The bladder is further provided with a plurality of longitudinally extending partitions forming a network of connected fluid retaining pockets. The fluid retaining pockets permitting the bladder to inflate such that pressure is applied to the palmar region of the constricted hand between three natural arches of the hand promoting restoration of the concave depression of the palm and a functional position of the hand.

19 Claims, 2 Drawing Sheets

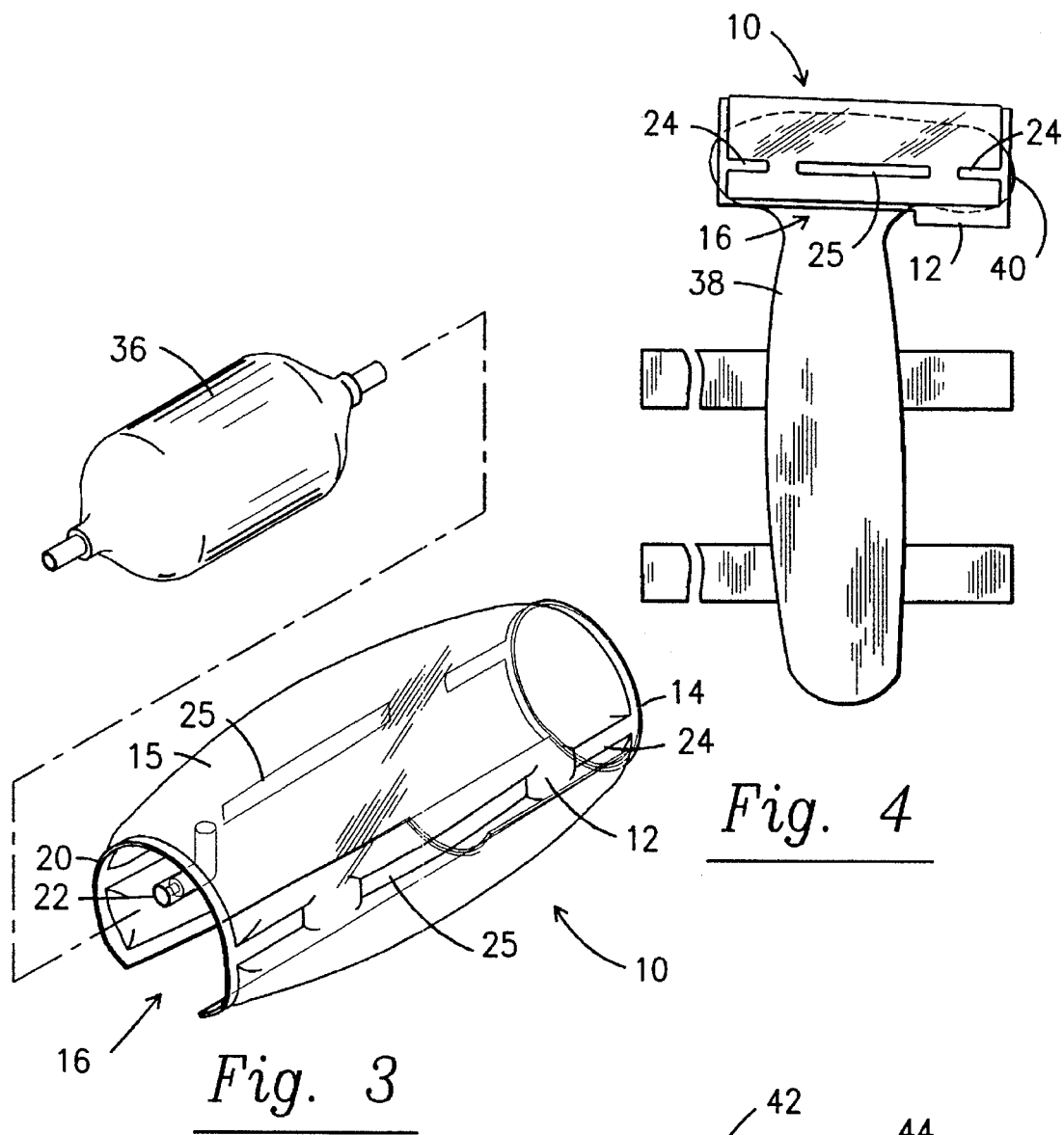
Fig. 3
Fig. 4
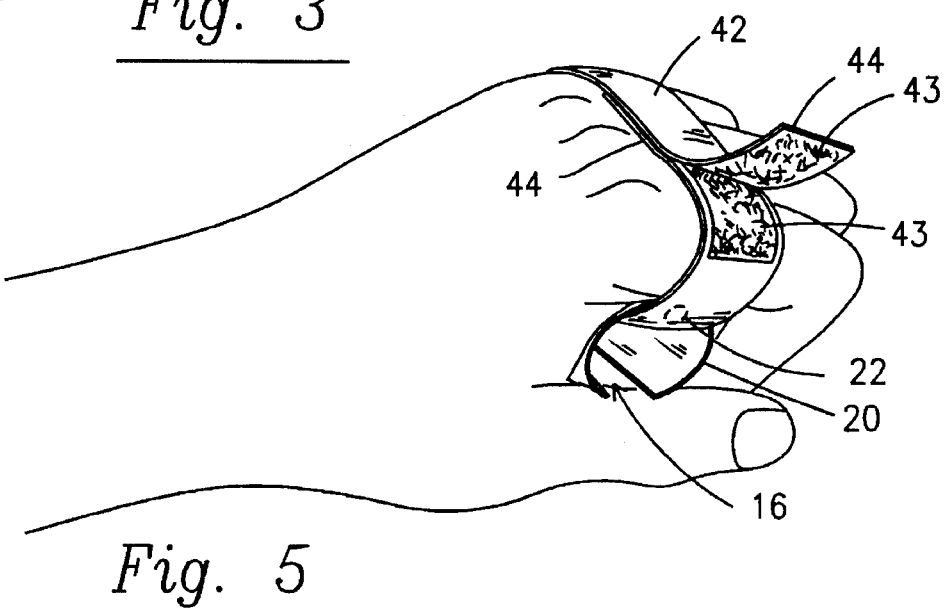
Fig. 5

INFLATABLE PALMAR BLADDER

BACKGROUND OF THE INVENTION

1. Field of the Invention

This invention relates to inflatable bladders for treating contractures of the wrist, hand, or fingers. More particularly, it relates to an inflatable palmar bladder for use with or without a wrist, hand, finger orthosis.

2. Description of Prior Art

Recently, the treatment of contractures of the wrist, hand, and fingers, has utilized orthosis devices having inflatable bladders, more particularly, air inflatable bladders. Some of these devices can been seen in U.S. Pat. Nos. 5,020,515 and 5,056,504.

The inflatable hand splints of U.S. Pat. Nos. 5,020,515 and 5,056,504 have been very effective for treating contractures of the wrist, hand, and fingers. These two subject patents have air bladders attached at a first end of the hand splint which is placed in the palm of the contracted hand. Air is pumped into the bladder for moving the fingers outwardly from the palmar portion of the hand, exercising the fingers, hand, and wrist. In the severely contracted hand, it is desirable to begin finger extension prior to treating the wrist. Accordingly, it would be advantageous to have an inflatable device for inserting within the palmar region of the severely contracted hand.

Attempts have been made to provide an inflatable hand orthosis in which the air bladder is inserted within the palm of a severely contracted hand. One such attempt can be seen in U.S. Pat. No. 5,152,740 wherein an inflatable bladder is provided for insertion into the palm of the severely contracted hand. Unfortunately, the hand splint of U.S. Pat. No. 5,152,740 is limited in that it can not be adapted to a static hand splint and therefore can not keep the fingers in an extended position after deflation of the bladder. There is no provision to attach the bladder to a static hand splint for treating contractions of the wrist. The 5,152,740 orthosis has straps disposed at opposed ends which merely prevent the bladder from slipping once air has been introduced into the bladder. Further, the air bladder in 5,152,740 merely extends the fingers away from the palm to a variety of coiled and partially coiled positions. The device does not work towards placing the hand in a functional position.

There exists a need to improve known inflatable hand orthosis to permit an inflatable bladder to be inserted within a severely contracted hand thereafter attaching a static hand orthosis without deflating the air bladder. The improved device should work towards placing the hand in a functional position and assist in restoring the arches of the hand and the natural concave shape of the palm.

SUMMARY OF THE INVENTION

I have invented an improved inflatable wrist, hand, finger orthosis incorporating an inflatable palmar bladder. The palmar bladder is detachable from a static hand orthosis permitting it to be used by itself for severe contractions of the hand or in conjunction with a wrist, hand, finger orthosis for other conditions of the wrist, hand or fingers.

The palmar bladder is substantially cylindrical in shape forming a roll having opposed open ends and a partial channel formed along a bottom portion of the bladder for receiving an end portion of a static hand splint. The palmar bladder further has a valve for connection to an inflating means.

My palmar bladder, detached from the splint, is inserted under the fingers within the palmar region of a severely contracted hand in a deflated state. Air is introduced into the bladder through the valve to extend the fingers outwardly thereby treating contracted fingers through low stretch therapy. A soft strap having a hook and loop closure mechanism is inserted through the opposed open ends of the bladder to secure the bladder to the back of the hand. Once the fingers are partially extended, a static hand splint can be attached to the palmar bladder permitting other conditions of the wrist, hand, and fingers to be treated. Once the static hand orthosis is set, the bladder can be removed, if desired, and replaced by a static fill.

The unique design of my palmar bladder allows the hand to work towards the functional position of the hand. The functional position of the hand is defined as the wrist extended 30 degrees from a line along the forearm, a normal transverse arch present, the thumb in abduction and opposition, and the proximal interphalanged joints flexed 45 degrees. The use of my device enhances the three natural arches of the hand, the transverse arch, the longitudinal arch, and the proximal arch. My device further approximates the fingers to the thumb after the functional position has been restored. Still further, in the process of restoring the functional position of the hand, my device helps restore the natural concave depression of a healthy hand. The concave depression is formed by the three arches of the hand. The concave depression is absent from a sick hand which has a flat palmar region due to the contractions. Still even further, my palmar bladder permits movement against the air resistance in the palmar bladder when inflated and thereby encourages exercise of the muscles and tendons of the wrist, hand, and fingers.

BRIEF DESCRIPTION OF THE DRAWINGS

The invention may be best understood by those having ordinary skill in the art by reference to the following detailed description when considered in conjunction with the accompanying drawings in which:

FIG. 3 is a perspective view of the inflatable palmar bladder illustrating where an air inflation device adapts thereto for inflating and deflating the palmar bladder;

FIG. 4 is a top plan view of a static hand wrist finger orthosis having the inflatable palmar bladder of the present invention adapted thereto.

FIG. 5 is a perspective view of a partially inflated palmar bladder of the present invention inserted within the palmar region of a contracted hand.

DETAILED DESCRIPTION OF THE INVENTION

Figure 1:
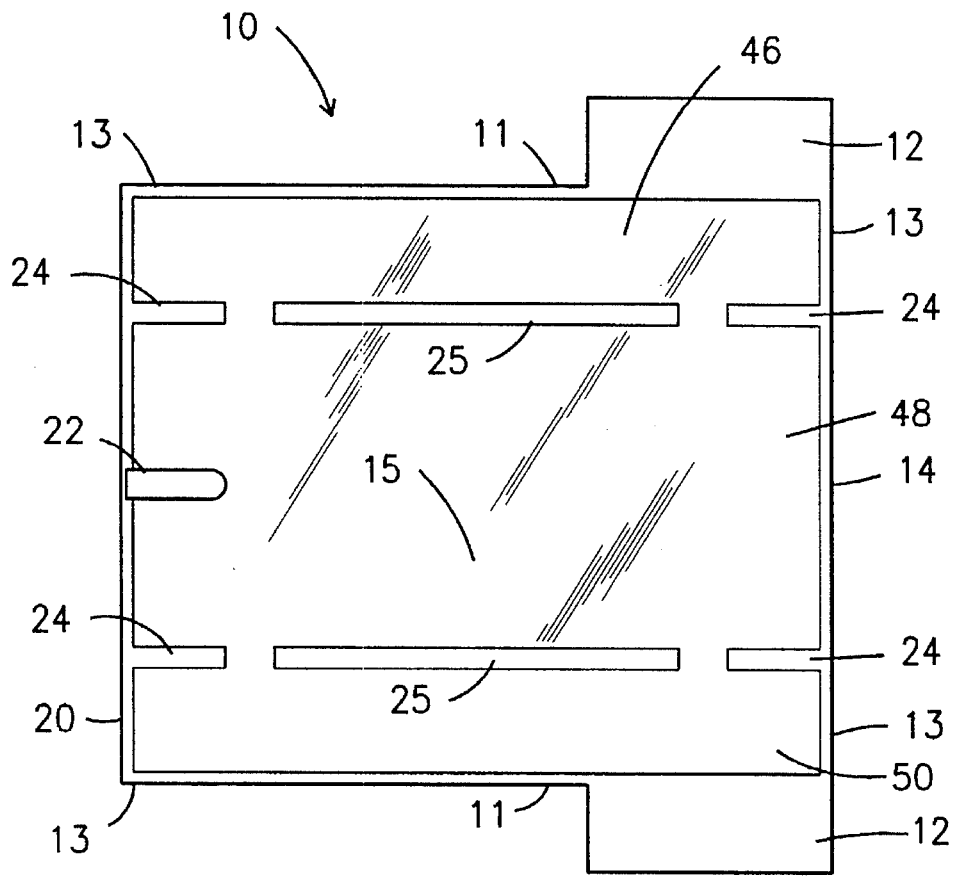
FIG. 1 is a top plan view of the inflatable palmar bladder of the present invention before it is sealed together.

Throughout the following detailed description, the same reference numerals refer to the same elements in all figures.

Figure 2:
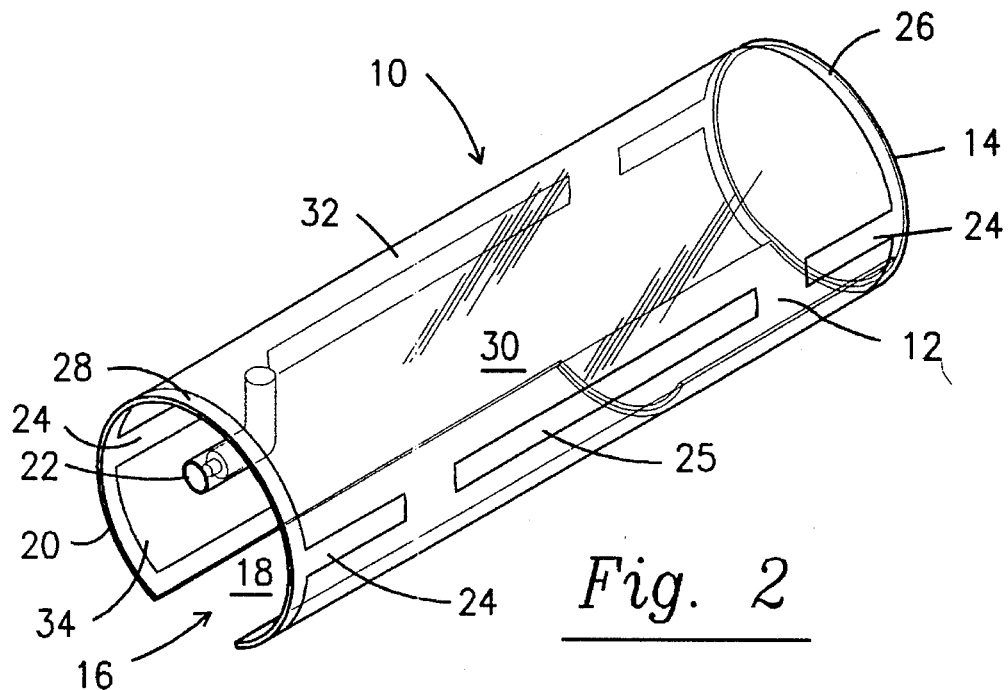
FIG. 2 is a perspective view of the inflatable palmar bladder after it has been sealed together to form its rolled shape.

Referring to FIG. 1, an inflatable palmar bladder 10 is provided having a pair of opposed tabs 12 projecting outwardly and attached along opposed side edges 11 at a first end 14. FIG. 1 depicts palmar bladder 10 in its manufactured flat form. Palmar bladder 10 is rolled together such that one of the opposed tabs 12 overlaps the other tab 12 and is thereafter sealed forming a cylinder or roll, as shown in FIG. 2. After tabs 12 are sealed together, a channel 16 is provided along a bottom portion 18 of palmar bladder 10, extending approximately two-thirds the length of palmar bladder 10 from a second end 20 distal to the sealed tabs 12. Further, after tabs 12 are sealed together, first and second ends, 14 and 20 respectively, are open. The preferred method of sealing tabs 12 together is through heat, although other known methods of sealing such as with an adhesive could be used to achieve the same result.

Palmar bladder 10 is made from two sheets of a soft and flexible material such as urethane. The sheets are heat sealed together along a peripheral edge 13 to form palmar bladder 10 thereby providing an interior area 15, as shown in FIG. 1. Interior area 15 is able to retain fluids which can be introduced and removed through a valve 22 located at second end 20. The preferred fluid to use with palmar bladder 10 is air. As shown in FIG. 2, palmar bladder 10 has a first set of sealed partitions 24 disposed at first and second ends, 14 and 20 respectively, extending longitudinally from a first and second edge 26 and 28 of first and second ends 14 and 20 respectively, towards a center 30. The positions of sealed partitions 24 at first and second edges 26 and 28 are such that interior area 15 surrounds three of four sides of sealed partitions 24. Additionally provided are a second set of sealed partitions 25 extending longitudinally between first and second edges 26 and 28 along the same longitudinal lines that the first set of sealed partitions 24 are positioned. The position of sealed partitions 25 are such that interior area 15 surrounds all four sides of sealed partitions 25. In the preferred embodiment, there is a first pair of sealed partitions 24 located along the first edge 26 oppositely positioned a second pair of sealed partitions 24 located along the second edge 28. Further to the preferred embodiment, a single pair of sealed partitions 25 are disposed between the opposed sealed partitions 24. Partitions 24 and 25 form a network of connected fluid retaining pockets within interior area 15. In the preferred embodiments partitions 24 and 25 from three connected fluid retaining pockets 46, 48, and 50, as shown in FIG. 1.

Sealed partitions 24 and 25 permit palmar bladder 10 to inflate such that interior area 15 increases in size applying pressure to the palmar region of the contracted hand to restore the concave depression in the hand and to extend the fingers of the patient outwardly from the palmar region. A soft cloth wrap (not shown) surrounding palmar bladder 10 permits palmar bladder 10 to retain a substantially cylindrical shape when a fluid is introduced therein. The cloth wrap additionally provides a comfortable surface for contact against the skin of the patient as well as a means to absorb any moisture between the palm and the fingers of the patient's hand.

Referring to FIG. 3, a ball pump 36 is used to inflate palmar bladder 10 by attaching to valve 22. It is understood that other pumps can be used to inflate palmar bladder 10 depending on the fluid introduced into palmar bladder 10 or the preference of a user.

Palmar bladder 10 is initially used without a static hand splint or a wrist, hand, finger orthosis when treating a severely contracted hand. Palmar bladder 10, fully deflated, is inserted within the palmar region of the severely contracted hand. Palmar bladder 10 can be used with either a left or right hand. Air is introduced through valve 22 by pump 36 thereby increasing the diameter of palmar bladder 10 and slowly extending the fingers of a patient outwardly by low stretch therapy. A soft strap 42 inserted through first and second end 14 and 20 respectively, as shown in FIG. 5, is wrapped around the back of the hand of the patient and secured by a hook and loop closure mechanism 43 sewn to opposed end portions 44 of strap 42. Strap 42 prevents palmar bladder 10 from slipping and covers valve 22 preventing accidental contact with any other part of the body of the patient.

Referring to FIG. 4, a wrist, hand, finger orthosis 38 can be easily adapted to palmar bladder 10 by inserting an end portion 40 of orthosis 38 into channel 16 of palmar bladder 10, Sealed tabs 12 provide a stop for end portion 40 when inserted into channel 16. Orthosis 38 is inserted once channel 16 is wide enough to accept end portion 40. The width of channel 16 will vary from patient to patient when air is introduced into palmar bladder 10. Therefore, the point at which orthosis 38 can be adapted to palmar bladder 10 will also vary from patient to patient.

A unique advantage of palmar bladder 10 is that it works the contracted hand towards the functional position of the hand. The palmar bladder 10 of the present invention is able to approximate the fingers to the thumb, enabling each finger to bend and touch the thumb, by extending the fingers outwardly and restoring the concave depression found in the palm of a healthy hand. The unique configuration of interior area 15 communicating with pockets 46, 48, and 50 formed by sealed partitions 24 and 25 applies pressure to the palmar region of the constricted hand while extending the fingers outwardly as fluid in introduced. This pressure caused by the expanding bladder 10 assists in the restoration of the concave depression. Further, when static hand orthosis 38 is attached to palmar bladder 10, additional pressure is provided to the palmar region by end portion 40 of orthosis 38.

Equivalent elements can be substituted for the elements employed in this invention to obtain the same results in the same manner.

Having thus described the invention what is claimed and desired to be secured by Letters Patent is:

1. An apparatus for facilitating the movement of the fingers of a patient's constricted hand, the apparatus comprising:

an inflatable bladder adapted for inserting into the palmar region of the patient's constricted hand, the inflatable bladder having a first end and a second end and being constructed from a top and bottom sheet of flexible material sealed together around a peripheral edge to form an interior area for retaining a fluid;

a pair of opposed tabs extending outwardly and attached to the first end of the inflatable bladder and permanently sealed together forming a longitudinal cylindrically shaped inflatable bladder;

a plurality of sealed partitions extending longitudinally along the inflatable bladder forming a network of connected fluid retaining pockets within the interior area;

an open channel formed by spaced apart peripheral edges of the inflatable bladder, the open channel being positioned from the second end of the inflatable bladder to the pair of opposed tabs for receiving an end portion of a static hand orthosis; and means for introducing and removing the fluid to and from the inflatable bladder.

2. The apparatus according to claim 1, comprising in addition, means adapted for attaching the inflatable bladder to the patient's constricted hand.

3. The apparatus according to claim 2, wherein the means adapted for attaching the inflatable bladder to the patient's constricted hand is a strap inserted through the first and second ends of the inflatable bladder, the strap having opposed end portions with hook and loop closure means attached thereto and adapted to be wrapped around a back side of the patient's constricted hand when the hook and loop closure means are engaged.

4. The apparatus according to claim 1, wherein the flexible material is urethane.

5. The apparatus according to claim 1, wherein one of the pair of opposed tabs is sealed over the top of the other.

6. The apparatus according to claim 1, wherein the means for introducing and removing the fluid to and from the inflatable bladder is a valve disposed along an end of the inflatable bladder.

7. An apparatus for facilitating the movement of the fingers of the patient's constricted hand, the apparatus comprising:

an inflatable bladder adapted for inserting into the palmar region of a the patient's constricted hand, the inflatable bladder having first and second ends including opposed side edges, respectively, being constructed from two sheets of flexible material sealed together around a peripheral edge to form an interior area for retaining a fluid;

a pair of opposed tabs attached along the opposed side edges of the first end of the inflatable bladder and permanently sealed together forming a longitudinally cylindrically shaped inflatable bladder;

a first set of sealed partitions disposed at the first and second ends of the inflatable bladder and extending longitudinally from a first and second edge of the peripheral edge respectively towards a center portion of the inflatable bladder;

a second set of sealed partitions disposed longitudinally between the first and second edge of the peripheral edge;

a channel formed by spaced apart peripheral edges along a bottom portion of the inflatable bladder, the channel being positioned from the second edge to the pair of opposed tabs for receiving an end portion of a static hand orthosis, the static hand orthosis having means for attachment to the patient for prohibiting the hand orthosis and the inflatable bladder from slipping away from the patient; and means for introducing and removing the fluid to and from the inflatable bladder.

8. The apparatus according to claim 7, wherein the first and second set of sealed partitions form three connected fluid retaining pockets within the interior area.

9. The apparatus according to claim 7, wherein the first set of sealed partitions comprises a first and second pair of sealed partitions located at the first and second ends respectively, the first pair of sealed partitions longitudinally and oppositely positioned from the second pair of sealed partitions.

10. The apparatus according to claim 9, wherein the second set of sealed partitions comprises a single pair of sealed partitions disposed between the longitudinally and oppositely positioned first and second pair of sealed partitions.

11. The apparatus according to claim 10, wherein the first and second set of sealed partitions form a network of connected fluid retaining pockets.

12. The apparatus according to claim 11, wherein there are three fluid retaining pockets.

13. The apparatus according to claim 7, wherein the second set of sealed partitions comprises a single pair.

14. The apparatus according to claim 7, wherein the means for attaching the orthosis to the patient is a plurality of straps attached to the orthosis, the straps having hook and loop closure mechanisms provided therewith and adapted to be wrapped around the arm of the patient when the hook and loop closure mechanisms are engaged.

15. The apparatus according to claim 7, wherein the means for introducing and removing the fluid to and from the inflatable bladder is a valve disposed along the inflatable bladder second end.

16. The apparatus according to claim 15, wherein the fluid introduced within the interior area is air.

17. The apparatus according to claim 16, wherein the air is supplied by an air pump connected to the valve.

18. A method for facilitating the therapeutic exercise of a patient's constricted hand, the steps comprising:

providing an inflatable bladder having first and second ends including respective opposed side edges and being constructed from two sheets of flexible material sealed together around a peripheral edge to form an interior area for retaining a fluid, a pair of opposed tabs attached along the opposed side edges of the first end of the inflatable bladder and being permanently sealed together forming a substantially cylindrical shaped inflatable bladder, a channel formed by spaced apart peripheral edges along a bottom portion of said inflatable bladder, said channel being positioned from the second end of the inflatable bladder to the pair of opposed tabs and means for introducing and removing the fluid;

inserting the inflatable bladder between the fingers and palm of the patient's constricted hand;

introducing the fluid into the interior area permitting the inflatable bladder to increase in diameter thereby extending the fingers away from the palm;

providing a static hand orthosis having an end portion attached substantially perpendicular to a body portion and a means for securing the static hand to the patient;

engaging the means for securing the static hand orthosis to the patient prohibiting the static hand orthosis and inflatable bladder from slipping away from the patient;

retaining an amount of fluid within the interior area of the inflatable bladder which is comfortable for the patient; and allowing the patient to move the fingers of the constricted hand against an air resistance in the inflatable bladder encouraging exercise of muscles and tendons in the patient's constricted hand.

19. The method of claim 18, wherein pressure is applied to the palm between a proximal arch, a longitudinal arch, and a transverse arch of the constricted hand when fluid is introduced into the interior area.

* * * * *